United States Patent [19]

Hughes

[11] 4,109,658
[45] Aug. 29, 1978

[54] NEEDLE HOLDING DEVICE WITH PICK-UP MEANS

[76] Inventor: Joe L. Hughes, 4981 Lake Fjord Pass, Marietta, Ga. 30060

[21] Appl. No.: 765,447

[22] Filed: Feb. 4, 1977

[51] Int. Cl.² .......................................... A61B 17/06
[52] U.S. Cl. .................................................... 128/340
[58] Field of Search ............... 128/334 R, 335, 340, 128/326; 112/169

[56] References Cited

U.S. PATENT DOCUMENTS

| | | | |
|---|---|---|---|
| 1,131,163 | 3/1915 | Saunders et al. | 128/340 |
| 1,876,792 | 9/1932 | Thompson | 128/340 |
| 2,327,353 | 8/1943 | Karle | 128/340 |
| 3,090,386 | 5/1963 | Curtis | 128/334 R |
| 3,946,740 | 3/1976 | Bassett | 128/334 R |

Primary Examiner—Dalton L. Truluck
Attorney, Agent, or Firm—James B. Middleton

[57] ABSTRACT

A needle holding device for a surgical needle during a suturing procedure, the device including a holding device for holding the needle while passing the needle through the material to be sutured, and a selectively movable pick-up device to grasp the point of the needle and pull the needle through the material to be sutured, the pick-up device being subsequently movable towards the holding device to transfer the needle for the next stitch.

7 Claims, 6 Drawing Figures

U.S. Patent  Aug. 29, 1978  4,109,658
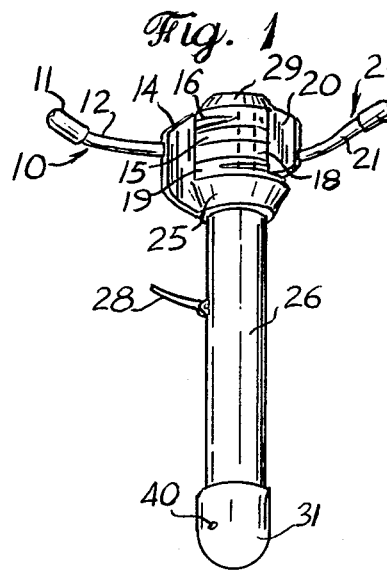
Fig. 1
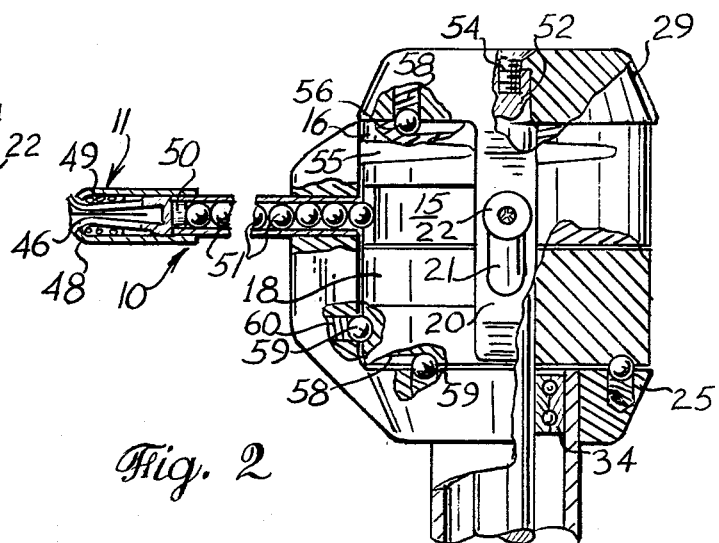
Fig. 2
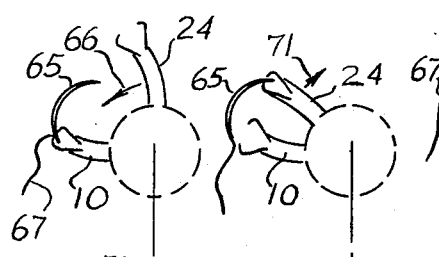
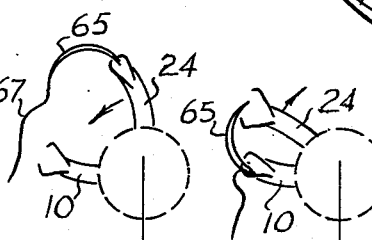
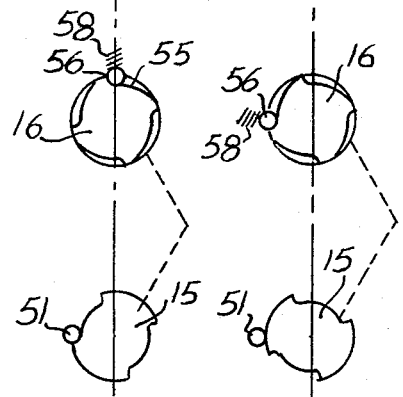
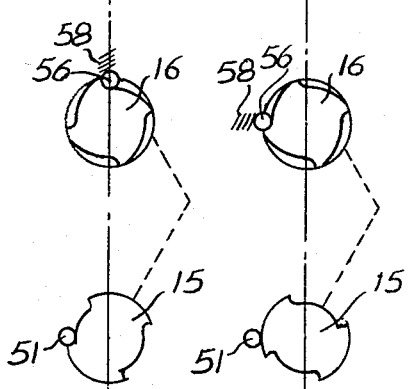
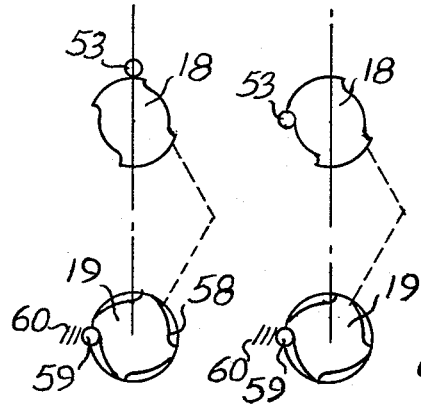
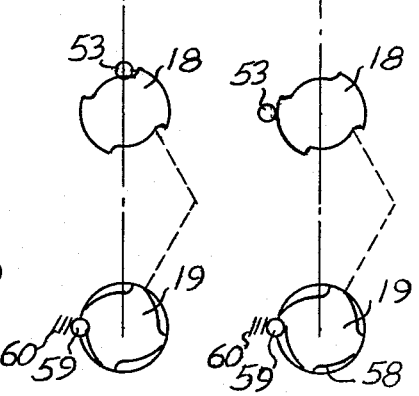
Fig. 3A  Fig. 3B  Fig. 3C  Fig. 3D

NEEDLE HOLDING DEVICE WITH PICK-UP MEANS

This invention relates generally to apparatus for suturing wounds, and is more particularly concerned with a needle holding device having needle pick-up means thereon and operable in conjunction therewith.

In many instances a wound must be held together by suturing, one common form of suturing being the sewing with a running stitch using a curved needle to pass through the tissue, the needle having suturing material attached thereto to form the stitches as the needle is passed successively through the tissue. The conventional technique for such suturing requires that the curved needle be placed into a needle holder, and the needle holder locked to retain the needle. The needle is then passed through the material to to be sutured while the material is held with a pair of forceps or the like. As soon as the point of the needle has passed through the tissue, the latch on the needle holder must be released, then the needle released from the needle holder leaving the needle unattended in the tissue. The point of the needle is grasped with "pick-ups" or the hands and pulled through the tissue, and the suturing material is pulled to the desired degree of tightness. The procedure must then be repeated, starting with placing the needle in the needle holder.

The conventional process for suturing is therefore quite inefficient and requires an excess amount of time, which is especially important when it is realized that the patient must remain anaesthetized for the entire time. Also, of course, the additional time of the surgeon is required for the routine matter when he could be occupied with other pressing matters.

The present invention overcomes the above mentioned and other difficulties with the prior art suturing apparatus and technique by providing a needle holding means having a needle pick-up means associated therewith and operable in conjunction with the needle holding means. Both the needle holding means and the needle pick-up means are operated by a pre-set programming means the form of camming means so that the entire apparatus is actuatable by a single motion by the operator. Thus, the present invention provides a needle holding apparatus for holding a needle with suturing material fixed thereto, the needle holding apparatus being operated from cam means for determining the appropriate gripping and releasing of the needle. A needle pick-up device is movable towards and away from the needle, and the needle pick-up device is operated from cam means for determining the appropriate gripping and releasing of the point of the needle. All of the action of the device is controlled by a single means for actuation by the surgeon, using only one hand.

The present invention therefore provides a novel and improved needle holder with a needle pick-up operable in conjunction therewith, the apparatus being actuatable with one hand for increased efficiency in suturing, and for more nearly sure control over the needle at all times.

These and other features and advantages of the present invention will become apparent from consideration of the following specification when taken in conjunction with the accompanying drawings in which:

FIG. 1 is a perspective view of a needle holding device made in accordance with the present invention;

FIG. 2 is an enlarged front elevational view of the embodiment of the invention shown in FIG. 1, portions of the apparatus being shown in cross-section; and, FIGS. 3A-3D are schematic illustrations showing the sequential operation of the device shown in FIGS. 1 and 2.

Referring now more particularly to the drawings, and to that embodiment of the invention here chosen by way of illustration, it will be seen in FIG. 1 of the drawings that the apparatus includes a needle holder generally designated at 10. The needle holder 10 includes a clamp 11 at the extending end of an operating tube 12, the tube 12 being carried by a needle holder boss 14. As will be discussed in more detail hereinafter, the operating tube 12 is longitudinally aligned with a needle holder cam 15 which is formed integrally with a position control cam 16.

Mounted co-axially with the cams 15 and 16, there is a needle pick-up cam 18 formed integrally with a position control cam 19. A needle pick-up boss 20 supports an operating tube 21 having a clamp 22 at its extending end. The needle pick-up is generally designated at 24.

The needle holder boss 14 is fixed to and supported by a collar 25, the collar 25 being carried at the end of a tubular handle 26. As will be seen more clearly hereinafter, there is a trigger 28 extending from the handle 26 for actuation of the device; and, when the trigger 28 is manipulated, the end collar 29 will be rotated with respect to the handle 26. The needle pick-up boss 20 is carried by the collar 29 so the boss 20 will move concentrically about the cams 15, 16, 18 and 19 to move the needle pick-up 24 towards the needle holder 10. During this motion, the controlled motion of the several cams will cause proper operation of the clamps 11 and 22 to manipulate a needle.

Attention is now directed primarily to FIG. 2 of the drawings for an understanding of the internal mechanism of the device. It will here be seen that the handle 26 comprises a tubular shell 30 extending from an annular collar 25 and having a cap 31 at the opposite end thereof. Along the longitudinal centerline of the shell 30 and coaxial therewith is a drive shaft 32. The drive shaft 32 is appropriately mounted for rotation within the shell 30, for example by bearings 34 in the collar 25 and bearings 35 adjacent to the cap 31.

The end 36 of the shaft 32 is bored to receive a torsion spring 38, the spring 38 being fixed to the shaft 32 at 39 as by a pin or the like and to the cap 31 by a pin 40. Because of this construction it will be understood that when the shaft 32 is rotated with respect to the shell 30 of the handle 26, the torsion spring 38 will be wound and will exert a force tending to return the shaft 32 to its original position; so, the shaft 32 oscillates in the device to effect the complete operation of the device.

Looking at the trigger 28 it will be seen in FIG. 2 that the trigger 28 is pivoted at 41 to the shell 30, and a spring 42 biases the trigger towards the position shown. Extending oppositely from the trigger 28, there is a pin 44 in operating engagement with a cam way 45, the cam way 45 extending helically around the shaft 32. From this construction it will be understood that, when the trigger 28 is moved rearwardly (towards the cap 31), the pin 44 will move forwardly, riding in the cam way 45 and causing the shaft 32 to rotate as the pin 44 moves down the cam way 45. As the pin 44 moves out of the cam way 45, the spring 38 will return the shaft 32 to its original position; then, when the trigger 28 is released, the spring 42 will return the trigger 28 to its original position. The pin 44 may engage the side of the cam way 45 and urge the shaft 32 in the opposite direction, but the cam follower means acting on the position control cam 16 will assure that the shaft 32 is properly located when the trigger 28 is released. It will of course be understood that other conventional means may be used to cause the partial rotation of the shaft 32.

The needle holder 10 is shown in cross-section in FIG. 2 to illustrate the operation thereof. The clamp 11 includes jaws 46 normally biased to move out, and the jaws 46 are held in by the surrounding housing 48. A spring 49 normally urges the jaws 46 into the housing 48, and a follower 50 can be used to urge the jaws 46 out of the housing. This is a conventional clamp arrangement and provides a clamp that can be opened by moving the follower 50 to urge the jaws 46 out of the housing 46 and allow the jaws 46 to open. When force on the follower 50 is removed, the spring 49 urges the jaws into the housing 46 to cause the jaws 46 to close. Of course, if an object, such as a needle, is placed in the jaws 46, the jaws will move under the influence of the spring 49 until the jaws are firmly closed on the object.

To operate the follower 50, there is a plurality of balls 51 free within the tube 12. It will be seen that the balls 51 are of such size and of such number that the balls 51 extend from the follower 50 to the surface of the cam 15. Thus, when the end-most ball 51 is on a low point of the cam 15, the follower 50 is in its inward position, allowing the jaws 46 to move under the influence of the spring 49; however, when the end-most ball 51 is on a high point of the cam 15, the balls 15 urge the follower 50 out, against the spring 49 to open the jaws 46.

While the foregoing discussion has been directed to the needle holder 10, it should be understood that the construction and operation of the needle pick-up 24 is substantially the same, so the pick-up 24 is not shown in detail and no further discussion of the operation of the needle pick-up is thought to be necessary. It should be pointed out, however, that the needle pick-up operating tube 21 is off-set to place the clamp 22 in the same transverse plane as the needle holder clamp 11. The balls 53 of course operate quite well around the curves to operate the clamp 22 as previously described with respect to clamp 11.

The cams 15, 16, 18 and 20 are generally annular in form, and are rotatable with respect to the drive shaft 32, it being understood that, in the embodiment of the invention here presented, the cams 15 and 16 are fixed with respect to each other, and the cams 18 and 19 are fixed with respect to each other. In each pair of cams, one cam acts as the operating cam (15, 18) and the other cam acts as the position control cam (16, 19).

It should first be realized that the collar 29 is fixed to the drive shaft 32 for rotation therewith. As here shown, the shaft 32 terminates in a square end 52 which is received within a mating hole in the collar 29. A screw 54 or other appropriate fastening means holds the assembly together. Thus, when the trigger 28 is manipulated to cause rotation of the drive shaft 32, the collar 29 is rotated, carrying with it the needle pick-up boss 20, hence the needle pick-up 24.

With the above in mind, it will be observed that the position control cam 16 has a plurality of cam surfaces 55 that have a maximum depth at one end and slope out to the surface of the cam. On each of these surfaces 55, there is a ball 56 urged against the surface 55 by a spring 58. Due to this arrangement, when the part carrying the ball 56 is rotated in one direction, the ball 56 will lock the cam 16 for rotation therewith; but, in the opposite direction, the ball 56 will roll up the gradual incline allowing the cam 16 to remain fixed. In FIG. 2, the ball 56 is shown in the collar 29, but it will be understood that additional balls 56 can be within the boss 20 and elsewhere as needed for sure operation. Also it should be understood that some such arrangements will be reversed to assure that the cam 16 does not move as other balls 56 roll up the sloped surface. It will therefore be understood by those skilled in the art that the cam 16 with the various balls 56 as cam followers constitutes a ratchet arrangement whereby the cam 16 is rotated when the collar 29 is moved in one direction, but the cam 16 remains fixed while the collar 29 is rotated in the opposite direction. Also, rotation of the cam 16 rotates the cam 15, moving different parts of the cam 15 by the needle holder 10 to cause the desired operation of the clamp 11.

The operation of the cams 18 and 19 is similar to the operation of the cams 15 and 16. There is a plurality of cam surfaces 58 having balls 59 with springs 60 to urge the balls 59 against the surfaces 58. The cam surfaces 58 have a maximum depth at one end, and slope gently to the surface of the cam 19 so that, effectively, a ratchet means is provided.

Turning now to FIGS. 3A–3D for a full description of the operation of the device, FIG. 3A shows the apparatus with a needle 65 and suturing material 67 grasped by the needle holder 10, and the needle pick-up 24 in its returned, or normal, position. The arrow 66 indicates the direction of motion of the pick-up 24 when the trigger 28 is pulled, and the cams are pictured with the various balls properly positioned.

The cam 16 has a ball 56 on a low portion of the cam. As a result, when the device is actuated to move the collar 29 and carry the ball 56, the cam 16 will be caused to rotate counterclockwise as viewed in the drawing. Since the cams 16 and 15 move together, the cam 15 will also be caused to rotate counterclockwise. As shown in FIG. 3A, the ball 51 is on a low portion of the cam 15 which allows the clamp to be closed to hold the needle 65.

The cam 18 is controlled by the cam 19, and it will be seen that a ball 59 is on a low portion of the cam 19; therefore, with rotational force directed counterclockwise as viewed in the drawing, the ball 59 will resist motion of the cam 19, hence the cam 18.

A ball 53 is shown on a high portion of the cam 18 so the clamp 22 is open. As the needle pick-up moves as shown by the arrow 66, the ball 53 will move the same way, which is counterclockwise as viewed in the drawing. Since the cam 18 is stationary, the ball 53 will roll around the cam to the position shown in FIG. 3B of the drawing.

FIG. 3B illustrates the device in the condition wherein the pick-up 24 has moved its limit so that the clamp 22 engages the point of the needle 65. Now, the trigger is to be released to cause the pick-up 24 to return to its normal position, but holding the needle 65 by the point. The next motion of the pick-up 24 is therefore as indicated by the arrow 71, or clockwise.

Since the motion of the balls 56 will be clockwise, it will be seen that the balls 56 will simply roll up the gradual slope of the cam 16, allowing the cam 16 to remain stationary. Since the cam 16 is stationary the cam 15 is also stationary.

It should be understood that, during the first motion of the cam 15, the ball 51 rolled along the uniformly low portion of the cam until the last portion of the motion. The cams are designed so that after the clamp 22 is over the point of the needle 65, the ball 51 reaches the high portion of the cam 15 to open the clamp 11. Substantially simultaneously with this motion, of course, the clamp 22 closes to grip the needle. Now, since the cams 15 and 16 are stationary during return of the pick-up 24, the ball 51 will remain on the high portion of the cam 15 to maintain the clamp 11 in its open position.

The balls 53 on cam 18 is on a low portion of the cam 18; and, as the pick-up 24 returns to its normal position, the cam 18 rotates so that the ball 53 remains in position, keeping the clamp 22 closed to grip the needle 65. The cam 18 rotates because the ball 59 on cam 19 is on a low portion of the cam 19 and the motion urges the ball 59 against the shoulder of the cam to cause the cam 19 to rotate with the ball 59. When the pick-up 24 has completely returned to its normal position, the arrangement is the same as shown in FIG. 3A except that the pick-up 24 is holding the needle by its point and the needle holder 10 has its clamp 11 open. This situation is shown in FIG. 3C, which will now be discussed along with the next motion.

It will be seen that the positions of the needle holder 10 and the pick-up 24 are both in their normal positions as shown in FIG. 3A, but the cams are rotated so that, in FIG. 3C the ball 51 is on a high portion of the cam 15 to open the clamp 11 while the ball 53 is on a low portion of the cam 18 to close the clamp 22. The next motion, then, is for the pick-up 24 again to move towards the needle holder 10; and, as before, the cam 16 causes the cams 15 and 16 to rotate while the cam 19 prevents rotation of the cams 18 and 19.

At the end of travel of the pick-up 24, the ball 51 falls to a low portion of the cam 15 and the ball 53 is moved to a high portion of the cam 18, thereby closing the clamp 11 and opening the clamp 22 as shown in FIG. 3D of the drawing.

Those skilled in the art should now understand that a needle 65 with suture material 67 carried thereby would be placed into the needle holder 10, the end of the needle having the suture material attached thereto entering the clamp 11. In this condition the needle 65 is passed through the material to be sutured until the point of the needle is exposed; then, the device is actuated causing the pick-up 24 to engage the point of the needle, and the clamp 11 of the needle holder 10 will release the needle while the clamp 22 of the pick-up 24 will grasp the needle. The pick-up 24 then returns to its normal position and the needle 65 is pulled entirely from the material being sutured.

Using only one hand, the surgeon again actuates the needle holder, and the pick-up 24 will move towards the needle holder 10 and insert the opposite end of the needle 65 into the clamp 11 of the needle holder 10. The clamp 11 will grasp the needle, the clamp 22 will release the needle, and the surgeon is ready to make another stitch.

It will therefore be seen that the needle holder device of the present invention provides for an efficient suturing technique, the device allowing actuation with only one hand of the surgeon to achieve complete control over the needle used for suturing. The needle is held at all times by the needle holding device so that a higher standard of sterility in the area of the wound can be maintained. The device of the present invention is rugged and durable, and is designed so that it can be subjected to the high temperature of an autoclave without damage to the device.

It will of course be understood by those skilled in the art that the particular embodiment of the invention here presented is by way of illustration only and is meant to be in no way restrictive; therefore, numerous changes and modifications may be made, and the full use of equivalents resorted to, without departing from the spirit or scope of the invention as defined by the appended claims.

I claim:

1. A needle holding device comprising a holding means for selectively grasping and releasing a first end of a surgical needle, a pick-up means for selectively grasping and releasing a second end of said needle, said pick-up means being adjacent to and movable towards and away from said holding means, actuating means for selectively moving said pick-up means towards and away from said holding means and camming means for determining when said holding means grasps and releases said first end of said needle and for determining when said pick-up means grasps and releases said second end of said needle, said holding means including a first clamp for receiving said first end of said needle and first operating means extending from said first clamp to said camming means, said pick-up means including a second clamp for receiving said second end of said needle and second operating means extending from second clamp to said camming means, said camming means including a first operating cam means, said first operating means including first cam follower means riding on said first operating cam means, said holding means being so constructed and arranged that, on motion of said first operating cam means, said first cam follower means will activate said first operating means to operate said first clamp, said camming means further including a second operating cam means, said second operating means including second cam follower means riding on said second operating cam means, said pick-up means being so constructed and arranged that, on motion of said second operating cam means, said second cam follower means will activate said second operating means to operate said second clamp.

2. A needle holding device as claimed in claim 1, said camming means further including a first ratchet means for controlling motion of said first operating cam means, and second ratchet means for controlling motion of said second operating cam means.

3. A needle holding device as claimed in claim 2, said pick-up means being movable in a first direction towards said holding means and in a second direction away from said holding means, said first ratchet means being so constructed and arranged that motion of said pick-up means in said first direction causes rotation of said first operating cam means in said first direction.

4. A needle holding device as claimed in claim 3, said second ratchet means being so constructed and arranged that motion of said pick-up means in said second direction causes rotation of said second operating cam means in said second direction.

5. A needle holding device as claimed in claim 4, said actuating means including a drive shaft, means for oscillating said drive shaft, a pick-up boss drivingly carried by said drive shaft for oscillation therewith, said pick-up boss carrying said second operating means.

6. A needle holding device as claimed in claim 5, said first operating means including a tube, and a plurality of balls free within said tube, one of said plurality of balls constituting said first cam follower means, said first operating cam means defining low portions and high portions thereon, the arrangement being such that when said one of said plurality of balls rides on one of said high portions of said first operating cam means, said plurality of balls within said tube causes opening of said first clamp, and when said one of said plurality of balls rides on one of said low portions of said first operating cam means, said plurality of balls within said tube allows closing of said first clamp.

7. A needle holding device as claimed in claim 6, said second operating means including a second tube, and a second plurality of balls free within said second tube, one of said second plurality of balls constituting said second cam follower means, said second operating cam means defining low portions and high portions thereon, the arrangement being such that when said one of said second plurality of balls rides on one of said high portions of said second operating cam means, said second plurality of balls within said second tube causes opening of said second clamp, and when said one of said second plurality of balls rides on one of said low portions of said second operating cam means, said second plurality of balls within said second tube allows closing of said second clamp.

* * * * *